United States Patent [19]

Sorkin

[11] Patent Number: 5,357,197
[45] Date of Patent: Oct. 18, 1994

[54] INDUCTIVE DEBRIS MONITOR WITH MULTI-TURN DETECTOR

[75] Inventor: Lev Sorkin, Fanwood, N.J.

[73] Assignee: Smiths Industries, N.J.

[21] Appl. No.: 974,242

[22] Filed: Nov. 10, 1992

[51] Int. Cl.⁵ ............... G01N 27/74; G01N 33/28; G01R 33/12
[52] U.S. Cl. .................. 324/204; 324/226; 324/236; 340/631; 73/61.42
[58] Field of Search ............... 324/204, 233, 226, 236, 324/442, 445, 446, 449, 636, 698, 650; 73/10, 861.08, 861.11, 61.42; 340/631; 333/219.1, 219.2

[56] References Cited

U.S. PATENT DOCUMENTS

| | | | |
|---|---|---|---|
| 4,926,120 | 5/1990 | Veronesi et al. | 324/204 |
| 5,001,424 | 3/1991 | Kellett et al. | 324/204 |
| 5,041,856 | 8/1991 | Veronesi et al. | 324/204 |

FOREIGN PATENT DOCUMENTS 2101330A  6/1981  United Kingdom ............... 324/204

Primary Examiner—Kenneth A. Wieder
Assistant Examiner—Jay M. Patidar
Attorney, Agent, or Firm—Anthony J. Casella; Gerald E. Hespos

[57] ABSTRACT

An inductive debris monitor for detecting chip-particles in tubing of a fluid wetted system. The inductive debris monitor includes a multi-turn detector and an electronic circuit having a resistor bridge configuration. The multi-turn probe detector wraps around the tubing of a fluid wetted system a plurality of times to detect the presence of the chip-particles while the electronic circuit analyzes and deciphers the detected chip-particle information.

8 Claims, 4 Drawing Sheets

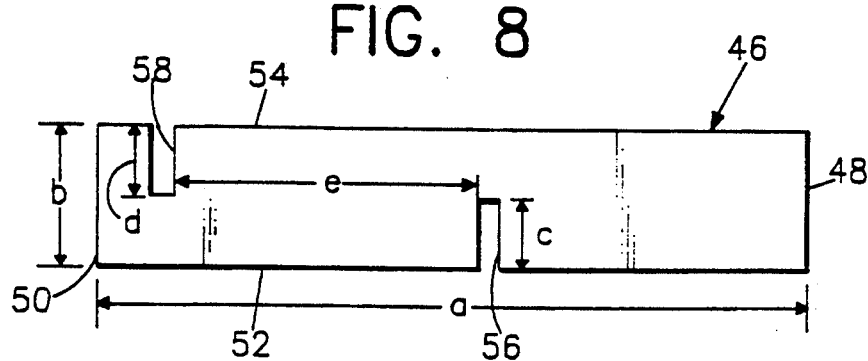
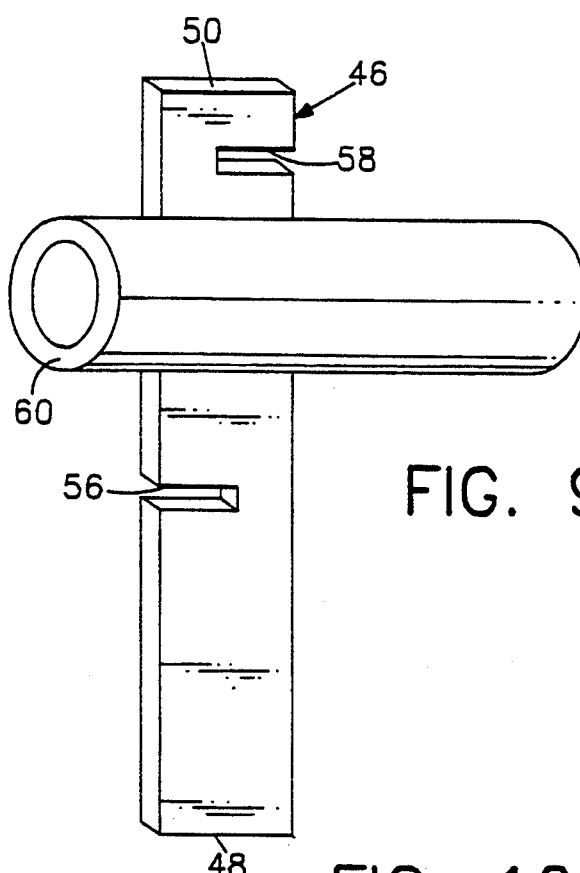
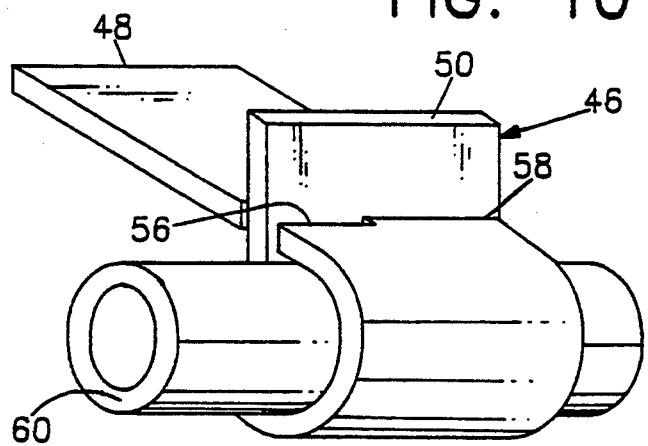

INDUCTIVE DEBRIS MONITOR WITH MULTI-TURN DETECTOR

BACKGROUND OF THE INVENTION

An Inductive Debris Monitor (IDM) detects and classifies particles which are present in a passageway of a fluid wetted system. In this respect, the IDM is especially, though not exclusively, concerned with the detection of metal chips or other particles, in an oil or other fluid line of a combustion engine.

The detected chips are categorized by size, rate of occurrence and whether they are magnetic or non-magnetic. This categorization of particles present in a fluid passageway provides a useful check on the status of the engine, and enables an early warning and identification of defects or malfunctions in an engine before those defects or malfunctions have serious consequences.

A prior art IDM is illustrated in FIGS. 1–3 and is identified generally by the numeral 10. The prior art IDM 10 comprises an inductive sensor 12 and an electronic circuit 14. The prior art inductive sensor 12 is placed along a fluid passageway 16 in a fluid wetted system, and connects to a transformer bridge 18 in the prior art electronic circuit 14. The transformer bridge 18 connects to a voltage control oscillator 20, a voltage controlled resistor 22, a pre-amplifier 24, an active amplifier 25 and a reactive error amplifier 26.

In use, alternating electric current is applied to the prior art inductive sensor 12 from the electronic circuit 14. The alternating current, tuned at the sensor resonant frequency, provides an electromagnetic field within the portion of the tubing 16 surrounded by the inductive sensor 12. This electromagnetic field is then monitored by the prior art electronic circuit 14 for any chip particles which may be present in a fluid flow contained within the portion of the tubing 16 being monitored by the prior art IDM 10. Chip particles that pass through the portion of the tubing 16 being monitored, cause a change in the inductance of the prior art inductive sensor 12. As shown by line "A" in FIG. 2, changes in phase angle relationships denote magnetic characteristics, while quantitative changes in the sensor inductance, as shown by line "B" with respect to voltage and time denote particle size. However, the transformer bridge 18 of FIG. 3 and other parts of the prior art electronic circuit 14 were prone to cause additional uncompensated phase shifts when correlated to temperature environments. Also, the exposure to high temperature environments quite often resulted in a reduction of sensor sensitivity. Further, the inductive sensor 12 of the prior art IDM 10 often had a low signal to noise ratio for small particles (e.g. less than 15 mil) caused by the spaced-apart relationship of the loops of the inductive coil 12 which surrounded the fluid passageway 16.

Another prior art IDM is shown in U.S. Pat. No. 4,926,120 which is issued to Veronesi. The prior art IDM of U.S. Pat. No. 4,926,120 includes a probe member which is illustrated in FIG. 4 herein, and which is identified by the numeral 28. The prior art probe member 28 is formed from a planar sheet 30 of a highly conductive metal which is wrapped partly around the outer circumference of a tube 31 containing the fluid flow to be monitored for chip particle detection. End portions 32 and 34 of the prior art probe 28 are bent to extend away from the tube 31 and are in spaced parallel relationship to one another. Capacitors 36 are interposed between the spaced end portions 32 and 34 of the probe member 28. The probe member 28 of FIG. 4 is advantageous over the coil 12 of FIG. 1, in that the probe member 28 of FIG. 4 reduces the signal-to-noise ratio. However, the probe member 28 of FIG. 4 has an undesirably low sensitivity, particularly for smaller particles. Further, the probe member 28 of FIG. 4 does not overcome the poor performance of the circuit 14 of FIG. 2 in high temperature environments.

Accordingly, it is an object of the present invention to avoid the disadvantages of the prior art.

More particularly, it is an object of the present invention to provide an inductive debris monitor which provides an increased sensitivity to chip particles having ferromagnetic and non-ferromagnetic characteristics.

Still another object of the present invention is to provide an inductive debris monitor which has lower loss of sensitivity compared to the prior art when subject to high temperature environments.

SUMMARY OF THE INVENTION

The subject invention is directed to an inductive debris monitor with improved sensitivity for detecting chip particles in a fluid wetted system, and with greater accuracy and predictability, in a high temperature environment. The subject inductive debris monitor comprises a sensor for detecting chip particles and an electronic circuit for analyzing any detected chip particles.

The sensor includes a multi-turn detector formed from an initially planar strip of metallic material which wraps around the circumference of a fluid passageway a plurality of times. Notches in opposed longitudinal edges of the strip enable this plural overlapping. Thus, portions of the multi-turn detector are in circumferentially overlapped relationship with other portions thereof. A flat flexible dielectric sheet is disposed between the circumferentially overlapped portions of the multi-turn detector. The two opposed ends of the multi-turn detector are separated by capacitors and are connected to electric leads which apply alternating electric current to the multi-turn detector. The alternating electric current thus enables the multi-turn detector to operate as a parallel tank circuit under the resonance which enables detection of ferromagnetic and non-ferromagnetic particles which may be present in the fluid passageway surrounded by the overlapping multi-turn detector. The deciphering and analyzing of this information is performed in an electronic circuit connected by the electric leads attached to the opposed ends of multi-turn detector.

The electronic circuit includes a resistive bridge as an input stage. The resistive bridge causes no additional phase shift, and therefore, there is no phase shift drift occurrence caused by high temperature environments which had been a problem in the prior art IDM described and illustrated above.

BRIEF DESCRIPTION OF THE DRAWINGS

FIG. 8 is a top plan view of a planar metal strip for forming the multi-turn detector of the subject invention.

FIG. 9 is a perspective view of the strip of FIG. 8 positioned adjacent a tube containing a fluid flow.

FIG. 10 is a perspective view of the multi-turn detector wrapped once around a tube.

DETAILED DESCRIPTION OF THE PREFERRED EMBODIMENTS

Figure 1:
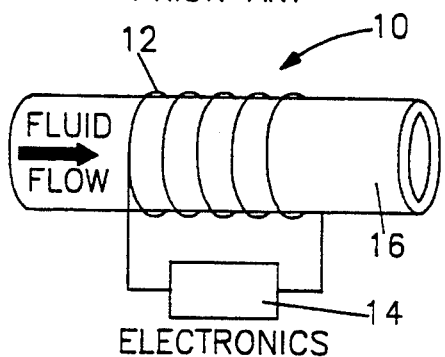
FIG. 1 is a simplified diagramic view of the prior art inductive debris monitor.
Figure 2:
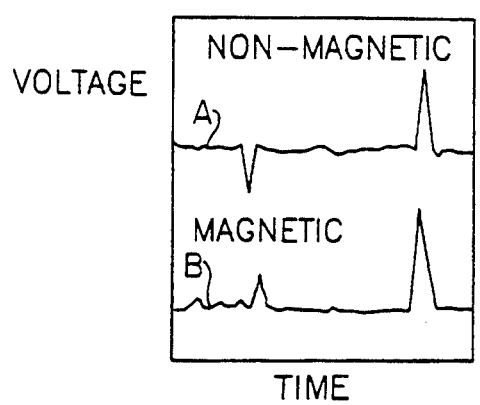
FIG. 2 is a graph depicting the magnetic and size characteristics of chip particles which are detected by the prior art inductive debris monitor.
Figure 3:
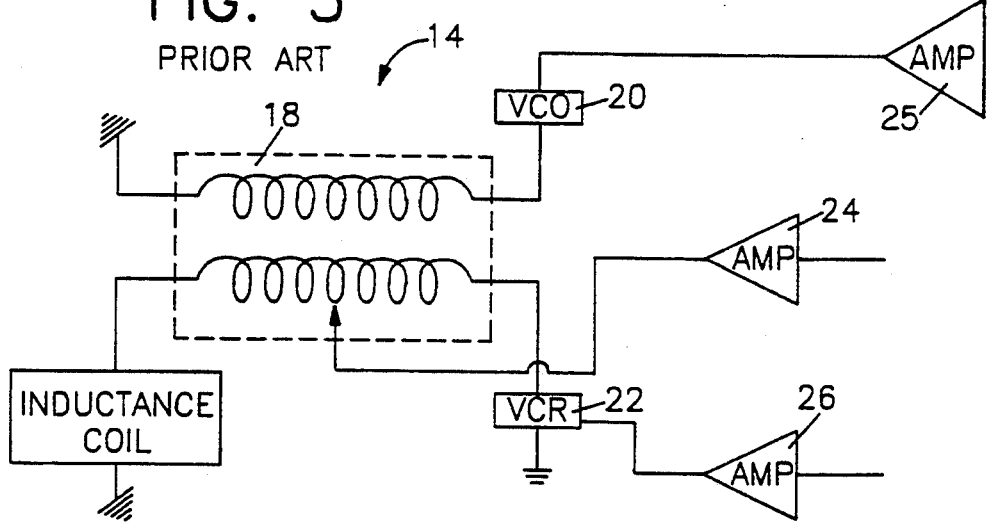
FIG. 3 is a diagramic view of the transformer bridge circuit of the prior art inductive debris monitor.
Figure 4:
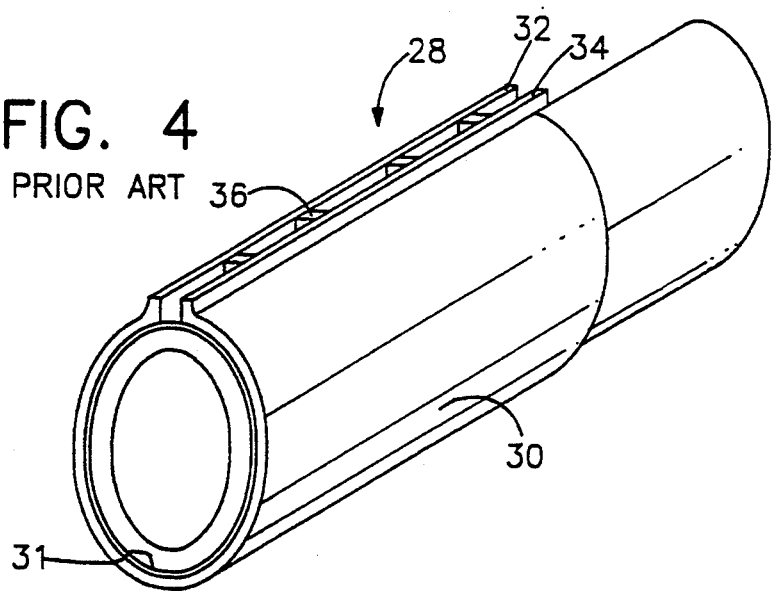
FIG. 4 is a perspective view of a probe member of a prior art inductive debris monitor.
Figure 5:
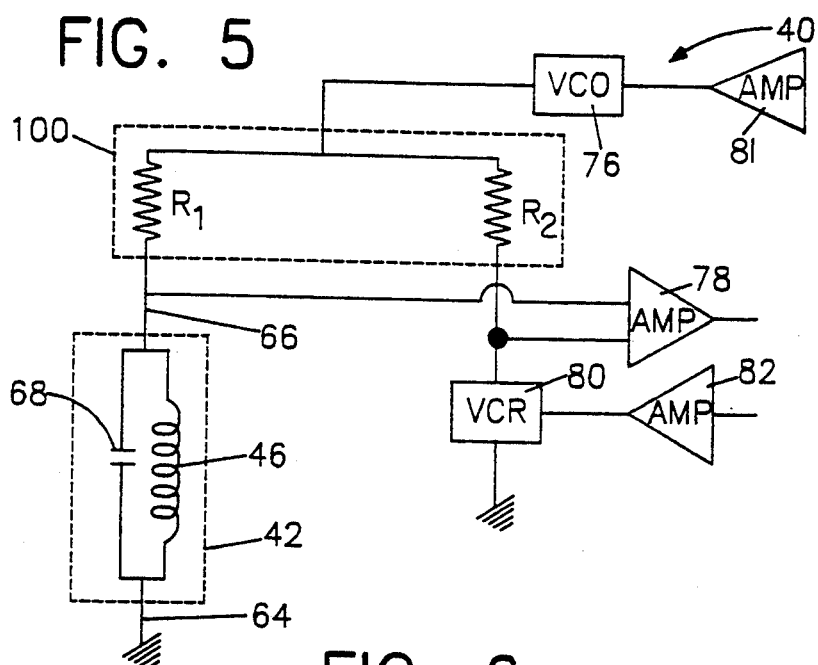
FIG. 5 is a simplified diagramic view of the resistor bridge circuit for the subject inductive debris monitor.

The inductive debris monitor of the subject invention is identified generally by the numeral 40 in FIG. 5. The inductive debris monitor 40 includes a multi-turn detector 42 which is illustrated schematically in FIG. 5 and which is shown in greater detail in FIGS. 6 and 7.

Figure 6:
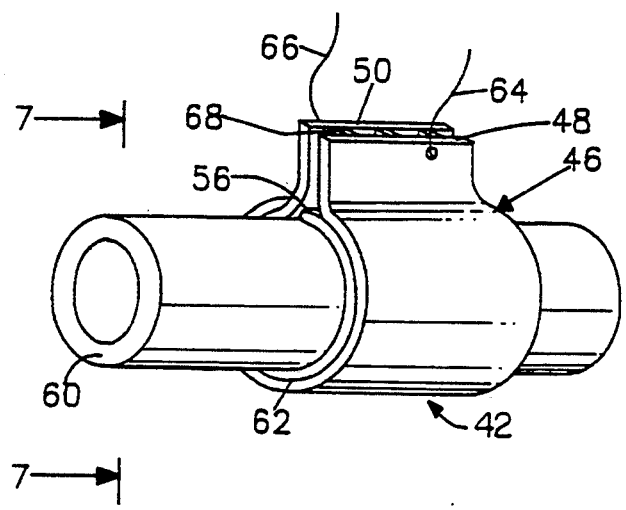
FIG. 6 is a perspective view of the multi-turn detector fully wrapped around a tube, such that the multi-turn detector strip overlaps itself.
Figure 7:
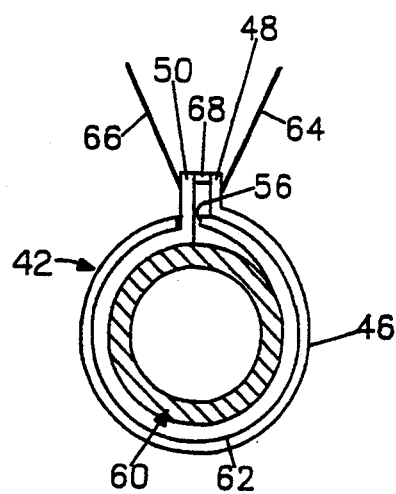
FIG. 7 is a cross-sectional view taken along line 7—7 of FIG. 6.

The multi-turn detector 42 of FIGS. 6 and 7 is constructed of an initially planar rectangular strip 46 of electrically conductive material, which is shown most clearly in FIG. 8. The strip 46 has opposed longitudinal ends 48 and 50 defining a length "a" which is a function of the diameter of a tube being monitored, and a function of the number of turns the strip 46 is to make around the tube. The strip 46 also has opposed longitudinal side edges 52 and 54 defining a width "b". Slots 56 and 58 extend respectively into the opposed side edges 52 and 54. The slots 56 and 58 define lengths "c" and "d" respectively, which are dimensioned such that the sum "c+d" is equal to or greater than the width "b" of the strip 46. The slots 56 and 58 are spaced from one another by a distance "e" which is equal to or slightly greater than the circumference around the tube being monitored.

The strip 46 wraps around a tube 60 carrying a fluid to be monitored in the manner shown sequentially in FIGS. 9, 10 and 6 respectively. More particularly, as shown in FIG. 9, the first end 50 of the strip 46 is disposed in proximity to the tube 60, such that the slot 58 is substantially adjacent the tube 60, and portions of the strip 46 between the slot 58 and the end 50 extend away from the tube 60. As shown in FIG. 10, portions of the strip 46 between the slots 58 and 56 are then wrapped around the tube 60, and the slot 58 is interengaged with the slot 56. Turning to FIGS. 6 and 7, portions of the strip 46 between the slot 56 and the end 48 are then wrapped an additional turn around the tube 60 with a thin flexible dielectric sheet 62 being disposed between the overlapped portions of the strip 46. Portions of the strip 46 generally adjacent the end 48 are bent into substantially spaced parallel relationship to the portions of the strip 46 between the slot 58 and the end 50. Conductive leads 64 and 66 are soldered or otherwise electrically connected to the ends 48 and 50 and capacitors 68 are electrically connected and interposed between the ends 48 and 50 of the strip 46 to define the completed detector 42 as shown most clearly in FIGS. 6 and 7.

The electric leads 64 and 66 will supply alternating electric current to opposed ends 48 and 50. Thus, the strip 46 of the multi-turn detector 42 functions as a parallel tank circuit with the capacitors 68. Because of the configuration of the strip 46 and the location of the capacitors 68, the parallel tank circuit defined by the multi-turn detector 42 multiplies the Q factor N times, where N is the number of turns. This high Q factor allows the parallel tank circuit defined by the multi-turn detector 42 to operate at higher sensitivity. Therefore, an overlay configuration of multi-turn detector maintains the advantage of a single turn detector from U.S. Pat. No. 4,926,120 of having a uniform electro-magnetic field within the tube 60, plus increases the tank sensitivity by multiplying the Q factor.

In addition, the dielectric between conductive layers creates a capacitor whose capacitance depends on the dielectric constant of the dielectric, the distance between the layers and the area covered by the layers. Selection of this dielectric and construction parameters may eliminate the need of the tank capacitors. Thus, any chip particles which may flow through the tube 60 will introduce an imbalance in the parallel tank circuit defined by the multi-turn detector 42, since the electromagnetic field provided by the parallel tank circuit will be disturbed by the presence of the metallic chip particles. Ferromagnetic chip particles will disturb the electromagnetic field of the parallel tank circuit differently from non-ferromagnetic metallic particles, since ferromagnetic and non-ferromagnetic metallic particles have different resulting phase angles. The magnitude of the disturbance of the electromagnetic field is dependent upon the size of the respective metallic chip particle.

Figure 11:
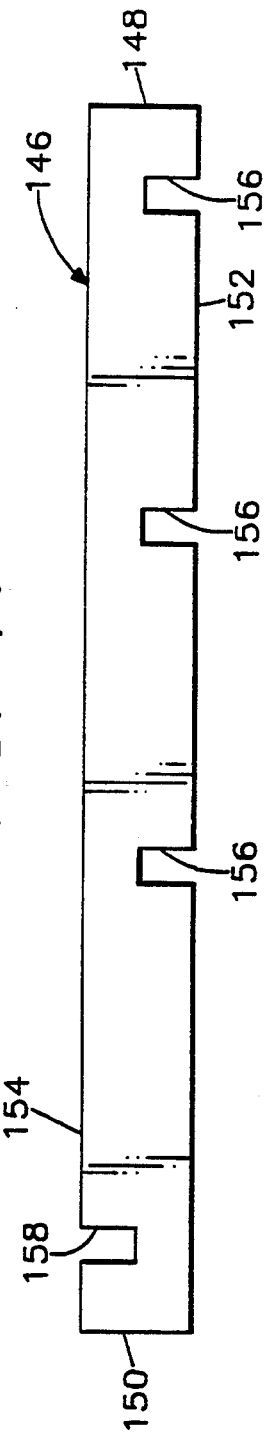
FIG. 11 is a top plan view of an alternate strip for a multi-turn detector.

An alternate strip for a multi-turn detector in accordance with the subject invention is shown in FIG. 11, and is identified by the numeral 146. The planar strip 146 preferably is of elongated rectangular shape with opposed longitudinal ends 148 and 150. The strip 146 also has opposed longitudinal sides 152 and 154. A slot 158 extends into a portion of side 154 adjacent to the longitudinal end 150. A plurality of slots 156 extend into side 152 at locations between slot 156 and the end 148. The distances between the slots 156 is a function of the diameter of the tube. The plurality of slots 156 enables the strip to overlap itself a plurality of times, with each slot 156 interengaging with the slot 158. This construction enables a higher overall sensitivity to particle detection.

An electronic circuit is used to analyze the information gathered from the detector 42. The input stage for this electronic circuit is shown in FIG. 5. The parallel tank circuit defined by the multi-turn detector 42 is represented by capacitor 68 and inductor 46. The electric lead 64 from the detector 42 is grounded, while the electric lead 66 is connected to a resistor bridge 100 defined by resistors $R_1$ and $R_2$. The resistor bridge 100 is connected to an amplifier 81 and a voltage controlled oscillator 76 which supplies an alternating electric current to the resistor bridge 100. The electric lead 66 and resistor $R_1$ connect to a preamplifier 78, while resistor $R_2$ connects to a voltage controlled resistor 80 which is connected to a resistive error amplifier 82.

In use, the multi-turn detector 42 of the inductive debris monitor 40 acts as a sensor which is instrumented as one half of an inductive bridge circuit with the inductance realized by the multi-turn detector 42 through which the monitored fluid passes. In the absence of metallic particles, the bridge is maintained in resonance and at balance. A chip particle is detected when the impedance of the sensor is changed as the chip particle passes through the induced electromagnetic field. This change in impedance moves the parallel tank circuit 68 and 46 out of resonance resulting in bridge imbalance, thereafter producing an electronic pulse. The magnitude of the pulse determines the relative size of the chip particle, while the phase shift relative to the carrier signal caused by the particle identifies the magnetic characteristics of the chip particle. The resistor bridge 100 of the input stage for the electronic circuit illustrated in FIG. 5 prohibits any additional phase shifts caused by the inductive components and also prohibits any phase drift caused by exposure to high temperatures, thereby avoiding a sensitivity loss as compared to the prior art transformer bridge. Furthermore, the phase-frequency dependence becomes monotonic in a working frequency range, thus providing a wider frequency capture range. IDM calibration will also no longer be required, and a higher sensor supply voltage can be used, since there are no transformer input voltage limitations with the resistor bridge 100.

Figure 12:
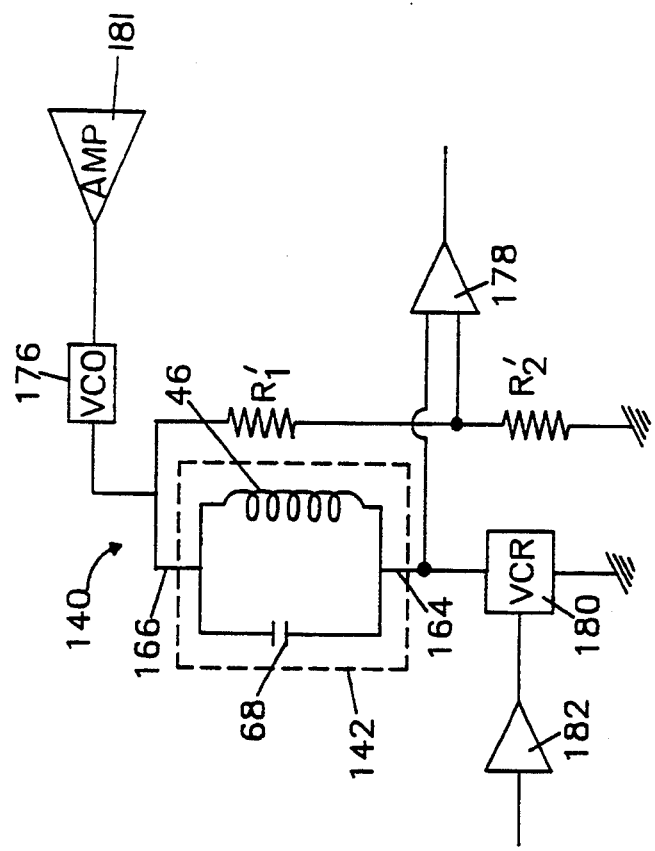
FIG. 12 is a simplified diagramic view of an alternative embodiment for the resistor bridge circuit of the subject invention.

An alternate construction of the input stage circuitry for the inductive debris monitor is shown in FIG. 12 and is identified by the numeral 140. The multi-turn detector 142 is substantially identical to the detector 42 described above. An electric lead 164 from the detector 142 is connected to a voltage controlled resistor 180 which is grounded, and which is also connected to a resistive error amplifier 182. An electric lead 166 connects to a voltage controlled oscillator 176, a phase error amplifier 181 and to a resistor bridge defined by resistors $R_1'$ and $R_2'$. The resistor bridge and the electric lead 164 further connect to a pre-amplifier 178. The alternate construction of the input stage for the electronic circuit illustrated in FIG. 12 enables the same advantages as provided by the input stage for the electronic circuit illustrated in FIG. 5.

Although the invention has been described with respect to a preferred embodiment, it is apparent that modifications can be made without departing from the scope of the invention as defined by the appended claims.

I claim:

1. A detector for an inductive debris monitor for detecting chip particles carried by a fluid in a tube, comprising:

an elongated strip of conductive material having opposed first and second ends and opposed first and second side edges, the first and second sides being provided respectively with first and second slots, said first slot extending into a portion of said first side in proximity to the first end such that a first narrow strip section is defined between said first slot and said second side of said strip, and said second slot extending into said second side at a location between said first slot and said second end such that a second narrow strip section is defined between said second slot and said first side of said strip, portions of said elongated strip from said first slot to said first end extending away from the tube, portions of said elongated strip from said first slot to said second slot being wrapped around the tube with said first narrow strip section being interposed between portions of said strip defining said second slot and with said second narrow strip section being interposed between portions of said strip defining said first slot, portions of the elongated planar strip from said second slot to said second end overlapping said portions of the elongated strip between the first and second slots, said second end being in spaced parallel relationship to said first end, and a dielectric material interposed between the overlapping portions of said strip.

2. A detector as in claim 1, wherein said strip is formed from an initially planar rectangular strip of conductive metal.

3. A detector as in claim 1, wherein said side edges define a width therebetween, and wherein said first and second slots define lengths, the sum of said lengths being at least equal to the width of the strip.

4. A detector as in claim 1, wherein the tube defines a circumference, the slots being spaced apart a distance at least equal to the circumference of said tube.

5. A detector as in claim 1, wherein the first slot extends into a portion of said first side in proximity to said first end, wherein and a plurality of second slots extend into said second side at locations between said first slot and said second end.

6. A detector as in claim 1, further comprising at least one capacitor electrically connected between the ends of the strip.

7. A detector for use with an inductive debris monitor for detecting chip particles carried by a fluid in a tube, comprising:

an elongated conductive strip having opposed first and second ends and opposed first and second side edges, the strip defining a first terminal portion adjacent the first end extending away from the tube, a first slot extending into a portion of the first side adjacent the first terminal portion such that a first narrow strip section is defined between said first slot and said second side edge of said strip, a tube engaging portion adjacent the first slot and extending circumferentially around the tube, at least one second slot extending into the second side at a location intermediate the tube engaging portion and the second end such that at least one second narrow strip section is defined between said second slot and said first side edge of said strip, said first narrow strip section being interposed between portions of said strip defining said second slot and said second narrow strip section being interposed between portions of said strip defining said first slot, at least one overlap portion intermediate the second slot and the second end circumferentially overlapping the tube engaging portion, said second end extending away from said tube in spaced relationship to said first end, a dielectric material interposed between said overlapping portions of said strip.

8. A detector as in claim 7, further comprising at least one capacitor electrically connected between the ends of the strip.

* * * * *